United States Patent [19]

Takeda et al.

[11] 4,398,037

[45] Aug. 9, 1983

[54] PROCESS FOR PRODUCING AROMATIC CARBOXYLIC ACIDS AND METHYL ESTERS THEREOF

[75] Inventors: Shinichi Takeda, Matsuyama; Masao Nonobe, Tokyo; Kenji Ishida, Matsuyama; Yorihiko Omoto, Kobe; Tatsuro Anno, Tokyo, all of Japan

[73] Assignee: Hercofina, Wilmington, N.C.

[21] Appl. No.: 319,770

[22] Filed: Nov. 9, 1981

[51] Int. Cl.$^3$ .................... C07C 67/08; C07C 51/265
[52] U.S. Cl. ........................ 560/77; 560/98; 560/100; 560/102; 560/103; 562/417; 562/421; 562/480; 562/492; 562/493
[58] Field of Search ................ 560/77, 103, 100, 102, 560/98; 562/417, 421, 480, 490, 492, 493

[56] References Cited

U.S. PATENT DOCUMENTS

| | | | |
|---|---|---|---|
| 1,900,648 | 3/1933 | Jaeger | 562/415 |
| 2,802,859 | 8/1957 | Fetterly | 560/77 |
| 2,833,816 | 5/1958 | Saffer et al. | 560/77 X |
| 3,060,222 | 10/1962 | Keller et al. | 560/77 |
| 3,790,624 | 2/1974 | Massie et al. | 562/416 |
| 3,873,611 | 3/1975 | Ichikawa | 562/417 X |
| 3,883,584 | 5/1975 | Ichikawa | 562/417 X |
| 3,890,374 | 6/1975 | Fujii et al. | 560/77 |
| 4,342,876 | 8/1982 | Klingman | 560/77 |
| 4,345,089 | 8/1982 | Nagura et al. | 560/77 |
| 4,346,230 | 8/1982 | Hoffmann et al. | 560/77 X |
| 4,354,037 | 12/1982 | Hirose et al. | 560/416 |

OTHER PUBLICATIONS

Chemical Abstracts, vol. 94:139461k, Apr. 27, 1981.

*Primary Examiner*—Natalie Trousof
*Assistant Examiner*—Vera C. Clarke
*Attorney, Agent, or Firm*—George H. Hopkins

[57] ABSTRACT

Disclosed is an improvement in the process for making an aromatic carboxylic acid or its methyl ester from an aromatic compound having at least one methyl or formyl group bonded directly to a nuclear carbon atom of the aromatic ring. The process comprises effecting oxidation of said compound in the liquid phase with molecular oxygen or a gas containing the same with a catalyst comprising a heavy metal compound, and in the substantial absence of an aliphatic carboxylic acid as a solvent, whereby a reaction mixture comprising the acid is formed. If the ester is desired, the acid then is esterified with methanol. The improvement comprises carrying out the oxidation in the co-presence of a lithium compound at a concentration of 0.1–10 moles per mole of heavy metal compound. The lithium compound is at least partly soluble in the reaction mixture or reacts with an acid component of the reaction mixture to form a lithium compound soluble in the reaction mixture.

9 Claims, No Drawings

PROCESS FOR PRODUCING AROMATIC CARBOXYLIC ACIDS AND METHYL ESTERS THEREOF

This invention relates to a process for producing aromatic carboxylic acids and methyl esters thereof in high yields. More specifically, this invention pertains to a process for producing an aromatic carboxylic acid or its methyl ester which comprises oxidizing at least one aromatic compound having at least one methyl or formyl group directly bonded to a ring carbon atom of its aromatic ring with molecular oxygen or a gas containing molecular oxygen in the liquid phase in the presence of a heavy metal catalyst, and if desired, esterifying the resulting oxidation reaction product containing the corresponding carboxylic acid with methanol.

Suitable aromatic compounds having at least one methyl or formyl group directly bonded to a ring carbon atom of the aromatic ring (to be referred to simply as starting aromatic compounds) are aromatic compounds having a benzene, naphthalene or biphenyl ring, especially the benzene ring. For commercial practice, toluene, p-xylene, p-toluic acid, p-tolualdehyde, methyl p-toluate, a mixture of p-xylene and methyl p-toluate, and a mixture of p-tolualdehyde and methyl p-toluate are preferred as the starting aromatic compounds.

Many methods have previously been known for producing aromatic carboxylic acids by oxidizing such starting aromatic compounds with molecular oxygen or a gas containing molecular oxygen (e.g., air).

Methods have also been known for obtaining methyl esters of aromatic carboxylic acids by esterifying the oxidation reaction product containing the aromatic carboxylic acid with methanol.

The present invention is specifically directed to the process which comprises oxidizing the aforesaid starting aromatic compound in the liquid phase with molecular oxygen or a gas containing molecular oxygen in the presence of a heavy metal catalyst. This process is carried out in the substantial absence of an aliphatic carboxylic acid such as acetic acid without using a halogen or a halogen compound, such as bromine, hydrogen bromide, ammonium bromide or sodium bromide, as a promotor. This is very advantageous because such halogen or halogen compounds, particularly bromine or bromine compounds, have the property of corroding the oxidation reaction apparatus.

Specific examples of such an oxidation process are as follows:

(1) Oxidation of toluene disclosed in British Pat. No. 1,430,830.

(2) Oxidation of p-xylene or p-toluic acid disclosed in British Pat. No. 1,234,009, and U.S. Pat. Nos. 3,883,584 and 3,873,611.

(3) Oxidation of methyl toluate disclosed in British Pat. No. 727,989.

(4) Oxidation of a mixture of p-xylene and methyl p-toluate disclosed in British Pat. Nos. 809,730 and 1,313,083, and U.S. Pat. No. 3,890,374.

(5) Oxidation of a mixture of p-tolualdehyde and methyl p-toluate disclosed in Japanese Patent Publication No. 23,493/65.

All of these processes (1) to (5) can be applied to the production of aromatic carboxylic acids in accordance with this invention.

The aromatic carboxylic acids and methyl esters thereof are useful as various raw materials or intermediates. Particularly, benzoic acid is useful as a food additive, and as a raw material for the production of epsilon-caprolactam, phenol, terephthalic acid and dyes. Terephthalic acid and dimethyl terephthalate are very useful industrial compounds for the production of fiber- or film-forming polyesters.

Accordingly, any process which can afford the aforesaid aromatic carboxylic acids or methyl esters thereof in high yields would be very valuable for commercial industrial purposes.

It is known that among the aforesaid processes for the aforesaid aromatic carboxylic acids or methyl esters thereof, a method involving the use of an oxidation catalyst comprising a cobalt compound and a manganese compound which are at least partly soluble in the oxidation reaction system, and a method involving the use of the aforesaid manganese compound and a nickel compound at least partly soluble in the oxidation reaction system can afford aromatic carboxylic acids or methyl esters thereof in relatively high yields. The details of the process which comprises oxidizing toluene, or a mixture of p-xylene and methyl p-toluate with molecular oxygen using a cobalt compound and a manganese compound as an oxidation catalyst are described in British Pat. Nos. 1,313,083 and 1,430,830. The details of the process involving oxidizing a mixture of p-xylene and methyl p-toluate with molecular oxygen using a manganese compound and a nickel compound as a catalyst are described in U.S. Pat. No. 3,890,374. The processes described in these British and U.S. Patents are also applicable to the process of the present invention.

Investigations of the present inventors have shown that aromatic carboxylic acids and oxidation intermediates thereof can be produced in higher yields by carrying out the oxidation in the co-presence of a suitable lithium compound in the processes which involve oxidizing at least one compound having at least one methyl or formyl group directly bonded to a nuclear carbon atom of the aromatic ring in the liquid phase with molecular oxygen in the presence of a heavy metal compound, particularly a heavy metal compound at least partly soluble in the reaction system, as a catalyst in the substantial absence of an aliphatic carboxylic acid solvent, including the processes described in the aforesaid British or U.S. Patents.

The suitable amount of the lithium compound is 0.1 to 10 moles per mole of the heavy metal compound.

It is an object of this invention therefore to provide a process for producing the aforesaid aromatic carboxylic acids or methyl esters thereof in higher yields than in the conventional processes for producing the aforesaid aromatic carboxylic acids or methyl esters thereof in the presence of a heavy metal compound as a catalyst.

Another object of this invention is to provide a process for producing aromatic carboxylic acids or methyl esters thereof at higher conversions and selectivities by carrying out the oxidation reaction at higher temperatures than in the conventional process for producing aromatic carboxylic acids or methyl esters thereof using a heavy metal compound as a catalyst.

Still another object of this invention is to provide a process for producing aromatic carboxylic acids or methyl esters thereof, in which the individual parts of a reaction apparatus including a heat exchanger or esterification tower are not clogged by the deposition of the heavy metal compound catalyst even when the concentration of the heavy metal compound in the oxidation reaction system is increased.

Further objects and advantages of this invention will become apparent from the following description.

The above objects and advantages of this invention are achieved by a process for producing aromatic carboxylic acids or methyl esters thereof which comprises oxidizing at least one aromatic compound having at least one methyl or formyl group directly bonded to a nuclear carbon atom of the aromatic ring in the liquid phase with molecular oxygen or a gas containing molecular oxygen in the presence of a heavy metal catalyst in the substantial absence of an aliphatic carboxylic acid solvent and without substantially using a halogen or halogen compound such as bromine or a bromine compound to form the corresponding aromatic carboxylic acid, and if desired, esterifying the oxidation reaction product containing the aromatic carboxylic acid with methanol, said oxidation reaction being carried out in the further presence of 0.1 mole to 10 moles, per mole of the heavy metal catalyst, of a lithium compound.

The lithium compound used in this invention is believed to act on the oxidation reaction as a co-catalyst.

The lithium compound used in this invention may be any lithium compound which is at least partly soluble in the oxidation reaction system of this invention, or any lithium compound which is insoluble but when added to the reaction system of this invention, reacts with a compound present in the reaction system such as carboxylic acids to be converted to a soluble lithium compound.

Examples of suitable lithium compounds for use in the process of this invention are listed below.

(i) Organic carboxylic acid salts (a) Salts of aliphatic carboxylic acids having 1 to 20 carbon atoms such as formic acid, acetic acid, propionic acid, butyric acid, palmitic acid, oleic acid, stearic acid and adipic acid, (b) salts of aromatic carboxylic acids having 7 to 20 carbon atoms such as benzoic acid, toluic acid, isophthalic acid, terephthalic acid, and monomethyl terephthalate, and salts of alicyclic carboxylic acids having 5 to 20 carbon atoms such as naphthenic acid, cyclohexane-monocarboxylic acid and methylcyclohexane-monocarboxylic acid.

(ii) Complex salts

Acetylacetonate complex salts, methylacetoacetate complex salts, and ethylacetoacetate complex salts.

(iii) Inorganic compounds

Lithium hydroxide, lithium oxide and lithium carbonate.

These lithium compounds are merely exemplary, and the invention is in no way limited to them. Other lithium compounds can be used if they are at least partly soluble in the oxidation reaction system and are convertible to soluble compounds when added to the oxidation reaction system. Metallic lithium can equally be used because it is converted to a soluble compound in the oxidation reaction system.

The lithium compound should be used in an amount of 0.1 mole to 10 moles per mole of the heavy metal compound used as the oxidation reaction catalyst. If the amount of the lithium compound is less than 0.1 mole, the effect of its use is not appreciable. On the other hand, when it is used in an amount exceeding 10 moles, the yield of the final product is rather lower than in the case of using only the heavy metal compound catalyst.

Advantageously, the amount of the lithium compound is 0.2 to 5 moles, especially 0.3 to 3 moles, per mole of the heavy metal compound catalyst.

Examples of the heavy metal compound used as a catalyst in this invention are soluble compounds of metals having variable valences such as cobalt, manganese, nickel and chromium. Among them, a catalyst comprising a cobalt compound, a catalyst comprising a cobalt compound and a manganese compound, and a catalyst comprising a manganese compound and a nickel compound are especially preferred for the practice of the process of this invention. It is especially advantageous to carry out the process of this invention in the presence of the catalyst composed of a cobalt compound and a manganese compound in combination with the lithium compound.

These cobalt, manganese or nickel compounds may be any cobalt, manganese or nickel compounds which are at least partly soluble in the oxidation reaction system of this invention, or are converted to compounds at least partly soluble in the reaction system, as described hereinabove with regard to the lithium compound. Organic acid salts, complex salts and inorganic compound salts of these metals corresponding to those described with regard to the lithium compound can be used. Suitable compounds are salts of cobalt, manganese or nickel with aliphatic carboxylic acids having 1 to 20 carbon atoms, especially lower aliphatic carboxylic acids such as acetic acid and aromatic carboxylic acids having a benzene ring such as benzoic acid, toluic acid and terephthalic acid.

These heavy metal compound catalysts can be used in concentrations and proportions usually known in the art. For example, in the case of a cobalt compound catalyst or a catalyst comprising a cobalt compound and a manganese compound, the cobalt compound is desirably used in an amount of 100 to 600 ppm, preferably 200 to 500 ppm, calculated as cobalt metal in the reaction mixture. It is especially preferred in the case of the catalyst comprising a cobalt and a manganese compound which is especially preferred in the present invention that the cobalt compound be used in the concentration within the above-specified ranges as cobalt metal in the reaction mixture, and the atomic ratio of cobalt metal to manganese metal be adjusted to 100:1 to 100:25.

Preferred aromatic compounds as starting materials in the process of this invention are toluene, p-xylene, p-toluic acid, p-tolualdehyde, methyl p-toluate, a mixture of p-xylene and methyl p-toluate, and a mixture of p-tolualdehyde and methyl p-toluate. A mixture of p-xylene and methyl p-toluate and a mixture of p-tolualdehyde and methyl p-toluate are especially preferred in the performance of the process of this invention. The processes using these aromatic compounds are generally called the Witten-Hercules process, and its details are described, for example, in British Pat. No. 1,313,083, and Japanese Patent Publication No. 23,493/1965.

The suitable weight ratio of p-xylene or p-tolualdehyde to methyl p-toluate in the starting mixture is from 1:4 to 4:1.

It is especially advantageous in this invention to perform the process in the presence of a combination of the catalyst comprising a cobalt and a manganese compound in combination with the lithium compound using a mixture of p-xylene and methyl p-toluate as a starting material.

The reaction temperature used to perform the process of this invention is in the range of 140° to 220° C. which is generally used in known conventional methods. The preferred temperature range is from 160° to 220° C. when the heavy metal compound catalyst comprises a combination of a cobalt and a manganese compound, and 170° to 220° C. when it comprises a combination of a manganese and a nickel compound.

In particular, when a mixture of p-xylene and methyl p-toluate is to be oxidized in the presence of the catalyst comprising a cobalt and a manganese compound, it is advantageous to employ an oxidation temperature of 160° to 200° C., above all 160° to 190° C. By performing this reaction in the copresence of the lithium compound in accordance with this invention, it is possible to produce monomethyl terephthalate and p-toluic acid and useful oxidation intermediates convertible to these compounds in higher yields than in the case of performing the reaction without the lithium compound. In particular, when the reaction of this invention is carried out at 160° to 190° C., monomethyl terephthalate, p-toluic acid and useful oxidation intermediates convertible to these compounds can be produced with higher conversions and selectivities of p-xylene and methyl p-toluate than in the case of performing the reaction in the presence of a catalyst composed of a cobalt and a manganese compound in the absence of the lithium compound.

The gas containing molecular oxygen used in the oxidation reaction of this invention may be a gaseous mixture of oxygen and an inert gas such as nitrogen, helium, argon and carbon dioxide. For example, an oxygen-containing gas diluted with an inert gas is used. Air is most readily available and economical.

The reaction pressure used in the reaction of this invention is atmospheric pressure to 250 kg/cm$^2$ as the total pressure, and 0.2 to 50 kg/cm$^2$ as the partial pressure of oxygen. When the partial pressure of oxygen is lower than 0.2 kg/cm$^2$, the rate of the oxidation reaction is decreased. On the other hand, increasing of the total pressure beyond 250 kg/cm$^2$ is not preferred because the cost of the apparatus increases enormously. The preferred partial pressure of oxygen is 0.4 to 5 kg/cm$^2$.

The present invention is advantageously applicable to the Witten-Hercules process which comprises the oxidation of a mixture of p-xylene and methyl p-toluate in the presence of a catalyst comprising a cobalt and a manganese compound.

In the Witten-Hercules process, the mixture of p-xylene and methyl p-toluate is oxidized with air in the liquid phase in the presence of a catalyst comprising a cobalt and manganese. Then, generally without separating the metal catalyst used in the oxidation reaction, the oxidation reaction mixture is esterified with methanol. Methyl p-toluate and dimethyl terephthalate in the esterification reaction mixture are separated by distillation, and the dimethyl terephthalate is sent to the subsequent purifying step. In the meantime, the methyl p-toluate is recycled to the oxidation reaction zone and is again subjected to the oxidation reaction together with p-xylene.

After the separation of methyl p-toluate and dimethyl terephthalate by distillation, the distillation residue contains the catalyst compounds. The catalyst compounds are recycled to the oxidation reaction zone either as such together with the distillation residue, or after they are isolated from the distillation residue by extraction or the like. In this way, the catalyst compounds are recycled. However, depending upon the conditions of the process step, the catalyst compounds recycled gradually deposit in the reaction system and makes it impossible to operate the process stably. This would result in great industrial losses.

The present inventors have found that the use of the lithium compound has the advantage of preventing the deposition of the oxidation catalyst.

Accordingly, when the process of this invention is applied to the Witten-Hercules process which comprises oxidizing a mixture of p-xylene and methyl p-toluate with air in the liquid phase in the presence of a heavy metal catalyst, and then esterifying the oxidation reaction product with methanol, the desired aromatic carboxylic acid or its methyl ester can be obtained in higher yields than in the case of not using the lithium compound. Moreover, the use of the lithium compounds prevents the deposition of the oxidation catalyst on the apparatus which may occur depending upon the conditions of the process, and the process can be stably operated. Accordingly, this is an especially preferred embodiment of this invention.

Even when the lithium compound is used as a cocatalyst in accordance with this invention, the esterification of the oxidation reaction mixture can be performed without any trouble by using the same esterification conditions as in the conventional processes. Furthermore, the lithium compound can be recovered together with the heavy metal compound catalyst, and recycled to the oxidation zone.

The process of this invention can of course be applied to the other processes described hereinabove, and similar effects can be achieved.

The following examples illustrate the present invention more specifically. It should be understood however that the present invention is not limited to these examples.

EXAMPLES 1 TO 5 AND COMPARATIVE EXAMPLES 1 TO 3

A 500 cc stainless steel autoclave equipped with a reflux condenser, a stirrer and a gas blow inlet was charged with 80 g of p-xylene (PX), 120 g of methyl p-toluate (MPT), 5 g of p-toluic acid (PTA), cobalt acetate, manganese acetate and lithium acetate. While stirring the mixture at high speed at a temperature of 170° C. and a pressure of 5 kg/cm$^2$.G, air was blown into the mixture so that the flow rate of the air at the exit was 1200 cc/min. at atmospheric pressure. After the absorption of oxygen began, the reaction was performed for 3 hours. After the reaction, the product was cooled, and withdrawn. The product was analyzed for composition, and the yield of effective products which are intermediates for dimethyl terephthalate (DMT) (i.e., compounds convertible to DMT by oxidation and/or esterification, such as PTA, monomethyl terephthalate (MMT) terephthalic acid (TA), p-methylbenzyl alcohol, p-methoxycarbonylbenzyl alcohol, p-tolualdehyde, p-formylbenzoic acid and its methyl ester) was calculated in accordance with the following equation.

$$\text{Yield of effective products (\%)} = \frac{\text{Moles of the resulting effective products}}{\text{Moles of PX and MPT consumed}} \times 100$$

The concentrations of the cobalt acetate and manganese acetate in the starting mixture were adjusted to 400 ppm (1.39 milligram-atom) and 24 ppm (0.09 milligram-atom) respectively as metals, and the amount of lithium acetate was varied as shown in Table 1 below.

For comparison, the above procedure was repeated without adding lithium acetate.

The yields of the effective products in these runs are also shown in Table 1.

TABLE 1

| Example (Ex.) or Comparative Example (CEx.) | Amount of lithium | | Li/heavy metal ratio | Yield of the effective products (mole %) |
|---|---|---|---|---|
| | mg-atom | ppm | | |
| CEx. 1 | 0 | 0 | 0 | 85.2 |
| CEx. 2 | 0.03 | 1 | 0.02 | 85.3 |
| Ex. 1 | 0.15 | 5 | 0.1 | 87.3 |
| Ex. 2 | 0.74 | 25 | 0.5 | 90.8 |
| Ex. 3 | 1.48 | 50 | 1 | 92.0 |
| Ex. 4 | 2.96 | 100 | 2 | 91.1 |
| Ex. 5 | 7.40 | 250 | 5 | 88.9 |
| CEx. 3 | 17.76 | 600 | 12 | 80.6 |

EXAMPLES 6 TO 10 AND COMPARATIVE EXAMPLES 4 AND 5

Using the same type of autoclave as used in Examples 1 to 5, experiments were carried out under the same conditions as in Examples 1 to 5 except that the amounts of cobalt acetate, manganese acetate and lithium acetate were changed as indicated in Table 2. The yields of the effective products obtained in these runs are shown in Table 2.

TABLE 2

| Example (Ex.) or Comparative Example (CEx.) | Amount of catalyst (mg-atom) | | | Li/heavy metal ratio | Concentration of catalyst in the starting mixture (ppm) | | | Yield of the effective products (%) |
|---|---|---|---|---|---|---|---|---|
| | Co | Mn | Li | | Co | Mn | Li | |
| Ex. 6 | 0.35 | 0.02 | 0.35 | 0.95 | 100 | 6 | 12 | 86.7 |
| Ex. 7 | 0.70 | 0.04 | 0.70 | 0.95 | 200 | 12 | 24 | 89.0 |
| Ex. 8 | 1.22 | 0.08 | 1.22 | 0.94 | 350 | 21 | 41 | 93.1 |
| Ex. 9 | 1.74 | 0.11 | 1.74 | 0.94 | 500 | 30 | 59 | 91.2 |
| Ex. 10 | 2.43 | 0.16 | 2.43 | 0.94 | 700 | 42 | 82 | 85.9 |
| CEx. 4 | 0.35 | 0.02 | 0 | 0 | 100 | 6 | 0 | 83.4 |
| CEx. 5 | 2.55 | 0.16 | 0 | 0 | 700 | 42 | 0 | 82.6 |

EXAMPLES 11 TO 14

Using the same type of autoclave as used in Examples 1 to 5, the same procedure as in Examples 1 to 5 was repeated except that the amounts of cobalt acetate and lithium acetate were set at 345 ppm (1.2 mg-atom) and 41 ppm (1.2 mg-atom) respectively as metals, and the amount of manganese acetate was changed as shown in Table 3. The yields of the effective products obtained in these runs are shown in Table 3.

TABLE 3

| Example | Amount of Mn (mg-atom) | Concentration of Mn (ppm) | Mn/Co gram-atomic ratio | Yield of the effective products (%) |
|---|---|---|---|---|
| 11 | 0.024 | 6 | 2/100 | 91.8 |
| 12 | 0.060 | 16 | 5/100 | 92.7 |
| 13 | 0.084 | 23 | 7/100 | 93.0 |
| 14 | 0.120 | 32 | 10/100 | 92.9 |

EXAMPLES 15 TO 21 AND COMPARATIVE EXAMPLES 6 AND 7

The same autoclave as used in Examples 1 to 5 was charged with 80 g of PX, 120 g of MPT and 5 g of PTA, and cobalt acetate, manganese acetate and lithium acetate as catalyst in a concentration of 350 ppm, 25 ppm, and 40 ppm, respectively as metals. The same reaction as in Examples 1 to 5 was carried out at each of the reaction temperatures indicated in Table 4. The yields of the effective products are shown in Table 4. For comparison, the above procedure was performed without using lithium acetate (Comparative Examples 6 and 7). The results are also shown in Table 4.

TABLE 4

| Example (Ce.) or Comparative Example (CEx.) | Reaction temperature (°C.) | Reaction time (hr) | Yield of the effective products (%) |
|---|---|---|---|
| Ex. 15 | 140 | 3.5 | 87.5 |
| Ex. 16 | 150 | 3.5 | 90.2 |
| Ex. 17 | 160 | 3.0 | 92.3 |
| Ex. 18 | 170 | 3.0 | 93.4 |
| Ex. 19 | 180 | 2.5 | 93.2 |
| Ex. 20 | 190 | 2.5 | 92.9 |
| Ex. 21 | 200 | 2.0 | 92.7 |
| CEx. 6 | 180 | 2.5 | 85.4 |
| CEx. 7 | 200 | 2.0 | 81.0 |

EXAMPLES 22 TO 26 AND COMPARATIVE EXAMPLES 8 TO 10

The same autoclave as in Examples 1 to 5 was charged with 70 g of PX, 130 g of MPT, 5 g of PTA and manganese acetate, nickel acetate and lithium acetate. While stirring the mixture at a pressure of 7 kg/cm$^2$.G and a temperature of 190° C., air was blown into it so that the flow rate of the air at the exit became 1500 cc/min. After the absorption of oxygen began, the reaction was performed for 3 hours. After the reaction, the reaction mixture was treated in the same way as in Examples 1 to 5, and the yield of the effective products was determined.

In the above experiment, the concentrations of manganese acetate and nickel acetate in the starting mixture were set at 200 ppm (0.746 mg-atom) and 200 ppm (0.698 mg-atom), respectively, as metal, and the amount of lithium acetate was changed as shown in Table 5.

For comparison, the above experiment was performed without using lithium acetate. The results are also shown in Table 5.

TABLE 5

| Example (Ex.) or Comparative Example (CEx.) | Amount of lithium | | Li/heavy metal ratio | Yield of the effective products (%) |
|---|---|---|---|---|
| | mg-atom | ppm | | |
| CEx. 8 | 0 | 0 | 0 | 84.8 |
| CEx. 9 | 0.03 | 1 | 0.02 | 85.0 |
| Ex. 22 | 0.14 | 5 | 0.1 | 87.4 |
| Ex. 23 | 0.72 | 24 | 0.5 | 90.1 |
| Ex. 24 | 1.44 | 49 | 1 | 91.5 |
| Ex. 25 | 2.89 | 98 | 2 | 91.4 |
| Ex. 26 | 7.22 | 244 | 5 | 90.4 |
| CEx. 10 | 17.33 | 587 | 12 | 83.2 |

EXAMPLES 27 TO 31 AND COMPARATIVE EXAMPLE 11

Using the same autoclave as in Examples 22 to 26, the same procedure as in Examples 22 to 26 was repeated except that the amounts of manganese acetate nickel acetate and lithium acetate were changed as shown in Table 6. The yields of the effective products are shown in Table 6.

TABLE 6

| Example (Ex.) or Comparative Example (CEx.) | Amount of catalyst (mg-atom) | | | Li/ heavy metal ratio | Concentration of catalyst in the starting mixture (ppm) | | | Yield of the effective products (%) |
|---|---|---|---|---|---|---|---|---|
| | Mn | Ni | Li | | Co | Ni | Li | |
| Ex. 27 | 0.28 | 0.26 | 0.54 | 1.0 | 75 | 75 | 18 | 90.2 |
| Ex. 28 | 0.37 | 0.35 | 0.72 | 1.0 | 100 | 100 | 24 | 91.1 |
| Ex. 29 | 1.12 | 1.05 | 2.17 | 1.0 | 300 | 300 | 73 | 90.4 |
| Ex. 30 | 1.87 | 1.75 | 3.62 | 1.0 | 500 | 500 | 123 | 88.8 |
| Ex. 31 | 2.61 | 2.44 | 5.05 | 1.0 | 700 | 700 | 171 | 85.6 |
| CEx. 11 | 2.61 | 2.44 | 0 | 0 | 700 | 700 | 0 | 82.7 |

EXAMPLES 32 TO 36

Using the same autoclave as used in Examples 22 to 26, the same procedure as in Examples 22 to 26 was repeated except that the amounts of manganese acetate, nickel acetate and lithium acetate were changed as shown in Table 7. The yields of the effective products obtained are shown in Table 7.

TABLE 7

| Example | Amount of catalyst (mg/atom) | | | Li/ heavy metal ratio | Concentration of catalyst in the starting mixture (ppm) | | | Yield of the effective products (%) |
|---|---|---|---|---|---|---|---|---|
| | Mn | Ni | Li | | Mn | Ni | Li | |
| 32 | 1.46 | 0.03 | 1.49 | 1.0 | 390 | 10 | 50 | 88.4 |
| 33 | 1.31 | 0.17 | 1.48 | 1.0 | 350 | 50 | 50 | 90.8 |
| 34 | 1.12 | 0.35 | 1.47 | 1.0 | 300 | 100 | 50 | 91.1 |
| 35 | 0.37 | 1.05 | 1.42 | 1.0 | 100 | 300 | 48 | 91.3 |
| 36 | 0.19 | 1.22 | 1.41 | 1.0 | 50 | 350 | 48 | 90.5 |

EXAMPLES 37 TO 41

The same autoclave as used in Examples 22 to 26 was charged with 70 g of PX, 130 g of MPT, 5 g of PTA and manganese acetate, nickel acetate and lithium acetate in a concentration in the stirring mixture of 200 ppm, 200 ppm and 50 ppm, respectively, as metals. The reaction was performed at each of the temperatures shown in Table 8. The yields of the effective products obtained are shown in Table 8.

TABLE 8

| Example | Reaction temperature (°C.) | Reaction time (hr) | Yield of the effective products (%) |
|---|---|---|---|
| 37 | 160 | 4.5 | 89.4 |
| 38 | 180 | 3.0 | 90.0 |
| 39 | 200 | 3.0 | 91.7 |
| 40 | 210 | 1.5 | 91.4 |
| 41 | 230 | 1.5 | 89.8 |

EXAMPLE 42

A mixture composed mainly of p-xylene and methyl p-toluate was oxidized in the liquid phase with air in the presence of (i) a mixture of cobalt acetate and manganese acetate or (ii) a mixture of nickel acetate and manganese acetate to form an oxidation reaction mixture containing p-toluic acid and monomethyl terephthalate as main ingredients.

The oxidation reaction mixture was then esterified with methanol to form an ester mixture containing methyl p-toluate and dimethyl terephthalate as main ingredients.

The concentrations of cobalt and manganese or manganese and nickel as metals in the ester mixture were as follows:

(i) Co=1003 ppm, Mn=61 ppm
(ii) Mn=1015 ppm, Ni=1014 ppm

One hundred grams of the ester mixture was fed into a 200 ml three-necked flask, and lithium acetate was added in an amount equal in gram-atom to the heavy metals. The mixture was maintained at 250° C. for 24 hours under sealing of $N_2$. Then, the ratio of the heavy metals deposited after the heating was calculated.

The presence or absence of lithium acetate and the ratio of the heavy metals deposited are shown in Table 9.

TABLE 9

$$\text{Ratio of heavy metals deposited (\%)} = \left(1 - \frac{\text{Amount of heavy metals dissolved after 24 hours}}{\text{Initial amount of heavy metals}}\right) \times 100$$

| Run No. | Addition of lithium acetate | Ratio of heavy metal deposited | | | Catalyst |
|---|---|---|---|---|---|
| | | Co | Mn | Ni | |
| 42-1 | No | 66 | 0 | — | (i) |
| 42-2 | Yes | 0 | 0 | — | (i) |
| 42-3 | No | — | 59 | 72 | (ii) |
| 42-4 | Yes | — | 17 | 29 | (ii) |

EXAMPLE 43 AND COMPARATIVE EXAMPLE 12

The same autoclave as used in Examples 1 to 5 was charged with 60 g of PX, 140 g of MPT and 5 g of PTA and as a catalyst, cobalt acetate and lithium acetate. While stirring the mixture at high speed at a temperature of 160° C. and a pressure of 4 kg/cm².G, air was blown into it so that the flow rate of the air at the exit became 1200 cc. The reaction was performed for 3.5 hours after absorption of oxygen began. After the reaction, the same procedure as in Examples 1 to 5 was performed, and the yields of effective products were determined.

The amounts of cobalt acetate and lithium acetate added in the oxidation experiment were 250 ppm (0.875 mg-atom), and 30 ppm (0.888 mg-atom), respectively, as metals in terms of their concentrations in the starting mixture.

For comparison, the same experiment as above was repeated except that lithium acetate was not added.

The yields of the effective products in these experiments are shown in Table 10.

TABLE 10

| | Amount of catalyst added (mg-atom) | | Concentration of catalyst in the starting mixture (ppm) | | Li/ heavy metal ratio | Yield of the effective products (%) |
|---|---|---|---|---|---|---|
| | Co | Li | Co | Li | | |
| Example 43 | 0.875 | 0.888 | 250 | 30 | 1.01 | 85.7 |
| Comparative Example 12 | 0.875 | 0 | 250 | 0 | 0 | 81.8 |

EXAMPLE 44 AND COMPARATIVE EXAMPLE 13

The same autoclave as used in Examples 1 to 5 was charged with 200 g of toluene, 5 g of benzoic acid, and as a catalyst, cobalt acetate, manganese acetate and lithium acetate in a concentration, as metal in the starting mixture, of 150 ppm (0.525 mg-atom), 5 ppm (0.019 mg-atom), and 15 ppm (0.443 mg-atom), respectively. While stirring the mixture at high speed at a temperature of 170° C. and a pressure of 7 kg/cm$^2$.G, air was blown into it so that the flow rate of the air at the exit became 1,500 cc/min. The reaction was performed for 3 hours after absorption of oxygen began. After the reaction, the reaction mixture was cooled, withdrawn, and analyzed for the amounts of benzoic acid, benzyl alcohol, benzaldehyde, benzyl benzoate and other products formed.

Benzyl alcohol, benzaldehyde and benzyl benzoate are intermediates to benzoic acid, and are evaluated as effective products. The yield of the effective products was calculated in accordance with the following equation.

$$\text{Yield (\%) of effective products} = \frac{\text{Total amount (millimoles) of benzoic acid and effective products}}{\text{Amount (millimoles) of toluene consumed}} \times 100$$

For comparison, the above procedure was repeated except that lithium acetate was not added.

The yields of the effective products in these experiments are also shown in Table 11.

TABLE 11

| | Amount of catalyst (mg-atom) | | | Concentration of catalyst in the starting mixture (ppm) | | | Li/heavy metal ratio | Yield of the effective products (%) |
|---|---|---|---|---|---|---|---|---|
| | Co | Mn | Li | Co | Mn | Li | | |
| Example 44 | 0.525 | 0.019 | 0.443 | 150 | 5 | 15 | 0.84 | 92.7 |
| Comparative Example 13 | 0.525 | 0.019 | 0 | 150 | 5 | 0 | 0 | 90.4 |

We claim:

1. A process for producing an aromatic carboxylic acid or its methyl ester, which comprises oxidizing in the presence of a catalyst consisting essentially of at least one heavy metal compound selected from the group consisting of those compounds of cobalt, manganese, nickel and chromium, that are at least partly soluble in the oxidation reaction mixture, but in the substantial absence of (a) an aliphatic carboxylic acid as a solvent, and (b) a halogen or a halogen compound, at least one aromatic compound in the liquid phase, having at least one methyl or formyl group directly bonded to a nuclear carbon atom of the aromatic ring, to form an oxidation reaction mixture comprising the corresponding aromatic carboxylic acid, and, if desired, esterifying with methanol the oxidation reaction mixture, said oxidizing being carried out in the co-presence of a lithium compound at least partly soluble in the oxidation reaction mixture and at a concentration per mole of said catalyst of 0.1 mole to 10 moles.

2. The process of claim 1 wherein said aromatic compound is at least one aromatic hydrocarbon selected from the group consisting of p-xylene, p-toluic acid, methyl p-toluate and p-tolualdehyde.

3. The process of claim 1 wherein said aromatic compound is a mixture of p-xylene and methyl p-toluate.

4. The process of any one of claims 1 to 3 wherein said heavy metal catalyst is either
   (1) a cobalt compound at least partly soluble in the reaction system,
   (2) a mixture of a cobalt compound at least partly soluble in the reaction system and a manganese compound at least partly soluble in the reaction system, or
   (3) a mixture of a nickel compound at least partly soluble in the reaction system and a manganese compound at least partly soluble in the reaction system.

5. The process of any one of claims 1 to 3 wherein said heavy metal compound catalyst is a mixture of (A) a cobalt compound at least partly soluble in the reaction system and (B) a manganese compound at least partly soluble in the reaction system, said cobalt compound being present in the reaction system such that the concentration of cobalt metal is 100 to 600 ppm.

6. The process of claim 5 wherein said cobalt compound and manganese compound are present in the reaction system such that the atomic ratio of cobalt metal to manganese metal is from 100:1 to 100:25.

7. The process of claim 6 wherein the oxidation reaction is carried out at a temperature of 160° to 200° C.

8. The process of claim 7 wherein the lithium compound is present in an amount of 0.2 mole to 5 moles per mole of said heavy metal compound catalyst.

9. A process for producing methyl esters of aromatic carboxylic acids consisting predominantly of dimethyl terephthalate and methyl p-toluate, which comprises contacting a mixture of p-xylene and methyl p-toluate in the liquid phase with molecular oxygen or a gas containing molecular oxygen at a temperature of 160° to 220° C. in the substantial absence of an aliphatic carboxylic acid solvent and a halogen or halogen compound in the presence of, as a catalyst, (A) a cobalt compound at least partly soluble in the reaction system and (B) a manganese compound at least partly soluble in the reaction system, and (C) a lithium compound at least partly soluble in the reaction system, the concentration of said cobalt compound in the entire reaction mixture being 100 to 600 ppm as metal, and the atomic ratio of cobalt metal to manganese metal being from 100:1 to 100:25, and the amount of said lithium compound being 0.1 mole to 10 moles per mole of the cobalt compound and manganese compound combined; and esterifying the oxidation reaction mixture with methanol.

* * * * *